(12) United States Patent
Friedrich et al.

(10) Patent No.: US 9,526,406 B2
(45) Date of Patent: Dec. 27, 2016

(54) ENDOSCOPIC INSTRUMENT

(71) Applicant: Karl Storz GmbH & Co. KG, Tuttlingen (DE)

(72) Inventors: Christina Friedrich, Eutingen (DE); Peter Schwarz, Tuttlingen-Nendingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 217 days.

(21) Appl. No.: 14/063,460

(22) Filed: Oct. 25, 2013

(65) Prior Publication Data
US 2014/0121460 A1    May 1, 2014

(30) Foreign Application Priority Data

Oct. 26, 2012 (DE) .................. 10 2012 110 255

(51) Int. Cl.
| | |
|---|---|
| *A61B 1/00* | (2006.01) |
| *A61B 1/005* | (2006.01) |
| *A61B 1/04* | (2006.01) |

(52) U.S. Cl.
CPC .......... *A61B 1/0052* (2013.01); *A61B 1/0016* (2013.01); *A61B 1/0057* (2013.01)

(58) Field of Classification Search
CPC .... A61B 1/0052; A61B 1/0057; A61B 1/0051
USPC ............... 600/140–150, 139; 606/1; 604/528
See application file for complete search history.

(56) References Cited

U.S. PATENT DOCUMENTS

| | | | |
|---|---|---|---|
| 4,499,895 A | 2/1985 | Takayama | |
| 4,503,842 A | 3/1985 | Takayama | |
| 4,721,099 A | 1/1988 | Chikama | |
| 5,060,632 A | 10/1991 | Hibino et al. | |
| 6,932,761 B2 | 8/2005 | Maeda et al. | |
| 7,331,924 B2 | 2/2008 | Arai et al. | |
| 2009/0076330 A1* | 3/2009 | Ashida .............. | A61B 1/0052 600/146 |
| 2009/0227841 A1* | 9/2009 | Miyako ............. | A61B 1/00039 600/139 |

(Continued)

FOREIGN PATENT DOCUMENTS

| | | |
|---|---|---|
| EP | 0078017 A2 | 5/1983 |
| EP | 1825801 A1 | 8/2007 |

(Continued)

*Primary Examiner* — Matthew J Kasztejna
*Assistant Examiner* — Rynae Boler
(74) *Attorney, Agent, or Firm* — Whitmyer IP Group LLC

(57) ABSTRACT

Endoscopic instrument with a control element, an instrument shaft, an adjustment element, a pull element and an actuator, and also with an intermediate element which is operatively connected to the control element and to the adjustment element, wherein the intermediate element has a first portion and a second portion, the first portion is connected to the second portion, the second portion has a greater bending resistance than the first portion, and the first portion has a measurement element for measuring a flexion of the first portion, wherein the adjustment element has a first abutment device, which defines a first movement range of the first portion relative to the adjustment element, and a second abutment device, which defines a second movement range of the second portion relative to the adjustment element, and the first movement range is smaller than the second movement range.

20 Claims, 6 Drawing Sheets

(56) References Cited

U.S. PATENT DOCUMENTS

| | | |
|---|---|---|
| 2010/0210908 A1 | 8/2010 | Ashida et al. |
| 2011/0009698 A1* | 1/2011 | Ashida ............... A61B 1/00006 600/118 |
| 2011/0065994 A1 | 3/2011 | Kudoh et al. |

FOREIGN PATENT DOCUMENTS

| | | |
|---|---|---|
| EP | 2039284 A1 | 3/2009 |
| EP | 2324755 A1 | 5/2011 |
| WO | 2012063880 A1 | 5/2012 |

\* cited by examiner

ENDOSCOPIC INSTRUMENT

BACKGROUND OF THE INVENTION

The present invention relates to an endoscopic instrument with a control section with a control element, further with an instrument shaft with an actuatable portion, wherein the instrument shaft is connected to the control section, an adjustment element, a pull element, which is mechanically coupled to the adjustment element and to the portion of the instrument shaft, such that a movement of the adjustment element may cause an actuation of the portion via a force transmission via the pull element, and further with an actuator, which is coupled to the adjustment element, such that an actuation of the actuator may cause a movement of the adjustment element by force transmission from the actuator to the adjustment element.

Endoscopic instruments with a flexible or rigid instrument shaft are used both in industry and also in medicine. For example, flexible endoscopes are used in veterinary medicine for gastro-endoscopic examination of large animals. These endoscopes often have, at a distal end of their instrument shaft, a distal end portion, which finishes in an endpiece. The endpiece represents the distal part of the endoscope that is inserted into the body to be examined. It usually has the distal end of an endoscope optical system and also some of the suction, flushing and instrument channels.

To be able to ensure the greatest possible flexibility as regards a spatial orientation of the endpiece during the examination, the end portion of the instrument shaft is usually designed to be deflectable. By a deflection, or general actuation, of the portion relative to the rest of the instrument shaft, in particular by bending or curving, a part of the instrument shaft, in particular the endpiece, may be given the desired orientation. During this deflection, a user has to proceed carefully in order to ensure that no damage is done to any tissue located around the end portion. It is therefore important that the actuation of the portion may be very precisely controlled.

In flexible and rigid endoscopes according to the prior art, the portion is deflected via a pull element, in particular via bowden cables. The pull element is connected to an adjustment element, in particular a steering gear. The pull element is often secured on a cord pulley or drum. By actuation of the control element on the control section of the endoscope, the adjustment element is moved. A rotary movement of the adjustment element results in a translational movement of the pull element. The movement of the pull element in turn results in a deflection of the portion.

U.S. Pat. No. 4,499,895 is directed at an electrical endoscope, which is controlled via a lever coupled to the adjustment element. When the lever is moved relative to the adjustment element, a flexion of the lever or a change in resistance of a potentiometer is detected and, in this way, the adjustment element is assisted by an actuator. However, the construction shown is very unwieldy and, in the event of a fault, requires a special release mechanism in order to be able to continue operating the endoscope.

U.S. Pat. No. 7,331,924 is directed at an electrical endoscope with a deflectable distal portion. The endoscope is controlled in this case using a track ball, of which the movement caused by the thumb or another finger of a user is detected by an electrical circuit. Depending on the rotary movement of the track ball, as chosen by the user, a deflection control system triggers a motor, which causes a movement of the pull element and therefore a deflection of the distal portion.

However, the disadvantage of an electrical endoscope of this kind is that the control feels less intuitive, since the control of an electrical endoscope, e.g. when the latter strikes against tissue, does not provide the kind of feedback, in the form of a counterforce on the control element, that a person receives when using mechanical endoscopes. These problems are also found in electrical endoscopes that are controlled using a joystick. In this connection, reference is made purely by way of example to the document U.S. Pat. No. 6,932,761. Electrical endoscopes also have the disadvantage that, in the event of a defect, it is difficult to withdraw them from the cavity in the body when the distal portion has been deflected.

In mechanical endoscopes, the portion is deflected exclusively by a mechanical force applied by the user to an external handle on the control section of the endoscope. For this purpose, the adjustment element is usually arranged fixedly on a shaft of the handle. When the user actuates the handle, this causes a rotary movement of the adjustment element and therefore in turn the translational movement of the pull element.

However, depending on the endoscope length and on the position of the instrument shaft, purely mechanical endoscopes may require considerable forces for actuating them. Moreover, the mechanical actuation of the portion automatically generates a certain restoring force in the direction of the non-deflected position (zero position) of the endoscope. Furthermore, during the deflection, the portion forms, together with the pull element, a spring/damper system which stores energy when tensioned and releases energy when relaxed. This may result in a start-up idle time or a slow-down in the deflection of the end portion. The effect of this is that, as regards the deflection he would like to confer on the portion in order to be able to view a certain location, the user may obtain this only approximately or iteratively.

It is therefore an object of the present invention to proceed from an endoscopic instrument of the type mentioned at the outset and to develop it in such a way that the user, while obtaining assistance in the control of the endoscope as in the case of an electrical actuation, does not have to do without mechanical feedback via the endoscope. A further object is to ensure that the endoscope may still be operated even in the event of a failure of the electrical control.

SUMMARY OF THE INVENTION

There is provided an aforementioned endoscopic instrument with an intermediate element, which is operatively connected to the control element and to the adjustment element such that a force applied to the control element by the user may be transmitted to the adjustment element via the intermediate element in order to move the adjustment element, wherein the intermediate element has a first portion and a second portion, the first portion is connected to the second portion, the second portion has a greater bending resistance than the first portion, and the first portion has a measurement element for measuring a flexion of the first portion, wherein the adjustment element has a first abutment device, which defines a first movement range of the first portion relative to the adjustment element, and a second abutment device, which defines a second movement range of the second portion relative to the adjustment element, and the first movement range is smaller than the second movement range.

The invention affords a number of special features, which are seen in particular in the design of the intermediate element and of the adjustment element and in the interaction between control element, intermediate element and adjustment element. In order to illustrate this, some examples of the different possible ways of actuating the endoscopic instrument are explained below.

The first option to be considered is that of operation purely by motor. Here, a user actuates the control element in such a way that the intermediate element moves slightly in relation to the adjustment element, in particular moves slightly in rotation. When the first portion is braked or stopped in its movement by the first abutment device, an at least slight bending of the first portion occurs, since the user continues exerting a force on the control element.

It will be noted at this point that, in the context of this application, the term flexion includes in particular a stretching and a shortening. Moreover, the term "force" is also intended to include a torque, since the latter results in particular from the length of a lever arm multiplied by a force.

The flexion of the first portion may be detected by the measurement element. It is advantageous if it is not simply the presence of a flexion that is detected, but also the direction of the bending, in particular whether it entails stretching or shortening. It is particularly preferable if the extent of the flexion is also determined, since this permits a conclusion concerning the force applied by the user.

From knowledge of the flexion, the actuation performed by the user may be inferred. In particular, the actuation direction chosen by the user and/or the force applied by the user may be detected. Since the actuation of the endoscopic instrument as desired by the user is thus detected, the actuator is then triggered in such a way that it moves the adjustment element in the manner desired by the user. The user then controls the endoscopic instrument purely by motor.

In a further possible operating mode, the adjustment element is acted on by a combination of motor actuation and force applied by the user. Once again, a flexion of the first portion leads to assistance by motor. Now, however, it is possible for the user to apply such great force that not only is the first portion in contact with the first abutment device, but also the second portion comes into contact with the second abutment device. Since the second portion has a greater bending resistance than the first portion, at least some of the force applied by the user is transmitted from the control element to the adjustment element via the intermediate element. This means that the movement of the adjustment element is effected both by the actuator and also by at least some of the force applied by the user. Moreover, it is thus possible to prevent a situation where the force applied by the user causes the first portion to undergo a plastic deformation that damages the first portion. The second portion thus constitutes an overload protection for the first portion.

As has already been explained, the second portion has a greater bending resistance than the first portion. It is preferable if the second portion has a much greater bending resistance than the first portion. It is advantageous if the bending resistance of the second portion is at least 1.5 times, preferably at least twice, particularly preferably at least three times, and in particular at least five times, the bending resistance of the first portion. The bending resistance is preferably to be understood as describing a relationship between an applied force and a resulting deformation, wherein the deformation is smaller at the same force and at a higher bending resistance. For example, this means that with two cuboids of equal length, but with different sizes of quadratic cross sections, the cuboid with the larger cross section has a greater bending resistance. A different bending resistance may preferably also be obtained through the choice of different materials for the first portion and the second portion, both in the case of identical or different geometries of first portion and second portion.

Finally, an actuation that is brought about exclusively by the force of the user, i.e. purely manually, should be considered. Here, it is assumed that the motor assistance by the actuator is not present. The reason for this may be a failure of the actuator or of its control system or, as is possible in a preferred embodiment, because the user has switched off the motor assistance. In this possible operating mode, a flexion of the first portion once again takes place, but no movement of the adjustment element by the actuator. It is therefore necessary that the second portion comes into contact with the second abutment device in order for at least most of the force applied by the user to be transmitted to the adjustment element.

As will be further explained on the basis of the illustrative embodiments, it is considered advantageous if the respective abutment device is formed by two projections on the adjustment element and if the respective portion moves between these two projections or bears thereon. In another advantageous embodiment, at least one of the abutment devices is designed as a recess or groove in the adjustment element, and the respective portion engages with a projection in this recess or this groove. In another advantageous embodiment, at least one abutment device is arranged as a projection on the adjustment element, and the end of the respective portion is configured in the manner of a fork with two prongs, wherein the projection is arranged between the prongs. Finally, in another advantageous embodiment, the abutment device is arranged as a projection on the adjustment element, and the projection engages in a recess or groove of the respective portion.

It will be noted that the adjustment element may have a plurality of component parts, in particular connection elements and force transmission elements, for example shafts, disks or toothed wheels. In a preferred embodiment, the adjustment element has a cord pulley or drum. In another preferred embodiment, the adjustment element also has a gear, with which a force applied to the adjustment element by the intermediate element is transmitted to the cord pulley.

It will finally be noted that it is advantageous if the material of the first portion is chosen such that the extent of the flexion is proportional to an applied force. It will also be noted that, in some embodiments, it is sufficient if the first movement range is only slightly smaller than the second movement range, since one of the aims is merely to prevent the movement of the adjustment element from taking place directly via the second portion, without flexion of the first portion occurring.

In a preferred refinement, the first portion and the second portion are formed in one piece, in particular made from exactly one material or material mix.

This permits cost-effective production and facilitates assembly. The bending resistances of the first portion and second portion may be defined by suitable choice of the material and dimensions of the respective portion, in particular length, height and width, and may be adapted to requirements. In particular, by suitable choice of the dimensions and/or of the material, it is possible to ensure that a deformation takes place only in the elastic range, and the portions are not permanently deformed and damaged.

In another refinement, the first portion is continuously in mechanical contact with the first abutment device.

This refinement is advantageous since, in this way, even very small auslenkungs of the control element may be detected.

In another refinement, the measurement element is arranged on the first portion, and the electrical resistance of the measurement element changes in the event of a change of shape of the measurement element.

Although provision is made, in a preferred embodiment, for the measurement element to be arranged inside the first portion, it is considered particularly advantageous if the measurement element is arranged on the first portion. This makes it possible in particular to design the intermediate element with regard to the desired bending resistances and/or geometric considerations and then to arrange a preferred measurement element on the first portion. The measurement element is preferably mounted on a side of the first portion on which a flexion may be particularly easily detected, i.e. particularly on surfaces that are stretched or shortened during flexion. Particularly suitable for this purpose are those surfaces which are at least approximately perpendicular to a direction of movement of the intermediate element. The measurement element is preferably configured as a strain gauge, which is mounted on the first portion. The first portion may also be understood as a flexural beam or bending beam.

In a refinement, the measurement element has a first measurement element part and a second measurement element part, which are arranged on two different sides of the first portion in such a way that, in the event of a flexion of the first portion, a change of shape of the first measurement element part differs from a change of shape of the second measurement element part.

In this refinement, a flexion may be detected particularly reliably and precisely. In addition, by virtue of the two measurement elements, it is possible to compensate for disturbances and environmental influences, for example resulting from a change in the ambient temperature. In this connection, it is advantageous to form a difference of a first measured value of the first measurement element part and of a second measured value of the second measurement element part. It is particularly advantageous if the two measurement elements are arranged on opposite sides of the first portion, the sides preferably being at least approximately perpendicular to a direction of movement of the intermediate element.

In another refinement, the second abutment device is adjustable in order to vary the second movement range of the second portion relative to the adjustment element.

In this way, it may be possible to individually adjust the extent to which a flexion of the first portion is to be possible before an at least partial transmission of force to the adjustment element via the second portion takes place. In some embodiments, it is advantageous to allow the second portion greater clearance, since this permits a more pronounced flexion of the first portion, and control purely by motor is therefore possible within a wide range. In other refinements, it is advantageous to keep the second movement range small, particularly if the aim is to ensure precision of the flexion measurement over the long term. It is thus possible to prevent a situation where the first portion bends too much and the precision of the flexion measurement suffers as a result. The abutment device is preferably adjusted by using abutment elements in which the position of an abutment surface may be changed, in particular by rotating, screwing or pushing.

In another refinement, the adjustment element has a gear, in particular a gear with a positive transmission ratio.

This refinement may permit particularly good adjustment of the extent to which the force applied by the user is transmitted to the pull element. It is particularly advantageous for the gear to be configured as a combination of external toothed wheel and internal toothed wheel. It will be noted at this point that, in another preferred refinement, the actuator has a gear.

In another refinement, a first rotation axis of the adjustment element and a second rotation axis of the actuator coincide.

This refinement may permit a cost-effective construction and simple transmission of force from the actuator to the adjustment element. In particular, a fifth rotation axis of a cord pulley and the second rotation axis of the actuator coincide.

In another refinement, the adjustment element has an at least approximately circular support element, on which the first abutment device and the second abutment device are arranged at least approximately in the circumferential direction of the support element.

This refinement may permit cost-effective production of the endoscopic instrument and reliable operation. In some embodiments, it is preferable if the support element is in direct mechanical contact with the pull element, and in particular if the support element is configured as a cord pulley. In other embodiments, particularly when using a gear, it is advantageous that the support element is not in direct mechanical contact with the pull element, in particular that the support element is a component separate from the cord pulley.

In another refinement a controller is configured to detect a measured value of a flexion of the first portion and to trigger the actuator on the basis of the measured value.

This refinement may permit an advantageous realization of the operation purely by motor or the combined operation. In connection with the measurement element, the controller evaluates a measured value or a measured signal which indicates a flexion of the first portion. This at least detects that the user wishes to actuate the endoscopic instrument. It is preferable also to determine the direction of the desired actuation and, in particular, also information concerning the force applied by the user. The controller accordingly receives information concerning the fact that the user actuates the endoscopic instrument and, preferably, concerning how he actuates it. The controller is therefore configured to trigger the actuator such that the actuation of the endoscopic instrument desired by the user is performed by motor or at least assisted by motor.

In another refinement, a third rotation axis of the control element and a fourth rotation axis of the intermediate element coincide.

This embodiment may permit a cost-effective construction and a simple transmission of force from the control element to the intermediate element.

In another refinement, the measurement element has at least one strain gauge.

This embodiment may permit simple detection of a flexion of the first portion. A voltage is preferably applied to the strain gauge, and the resulting current changes in the event of a flexion of the first portion, since the strain gauge is stretched (or shortened) and thus changes its electrical resistance. This embodiment is advantageous, among other reasons, because the measurement by means of a strain gauge can be performed easily and reliably. In some refinements, it is advantageous if both the first measurement element part and also the second measurement element part are each configured as strain gauges. In another advantageous embodiment, at least one polymer conductor is integrated into the portion to be bent, and the flexion is detected via the change of resistance.

In another refinement, the first portion and the second portion are configured at least approximately in a beam shape, converge on a common point and, in relation to this common point, are at an angle to each other.

This refinement may be easy to implement, particularly as regards an advantageous direct connection of first portion and second portion. It is preferable if the first portion and second portion actually touch at the common point, although other embodiments may be advantageous in which first portion and second portion are connected, for example, via a bridge or a common holder.

BRIEF DESCRIPTION OF THE DRAWINGS

It will be appreciated that the aforementioned features and the features still to be explained below can be used not only in the respectively cited combination, but also in other combinations or singly, without departing from the scope and spirit of the present invention.

Exemplary embodiments are explained in more detail in the following description and are shown in detail in the drawing, in which.

DETAILED DESCRIPTION OF THE INVENTION

Figure 1:
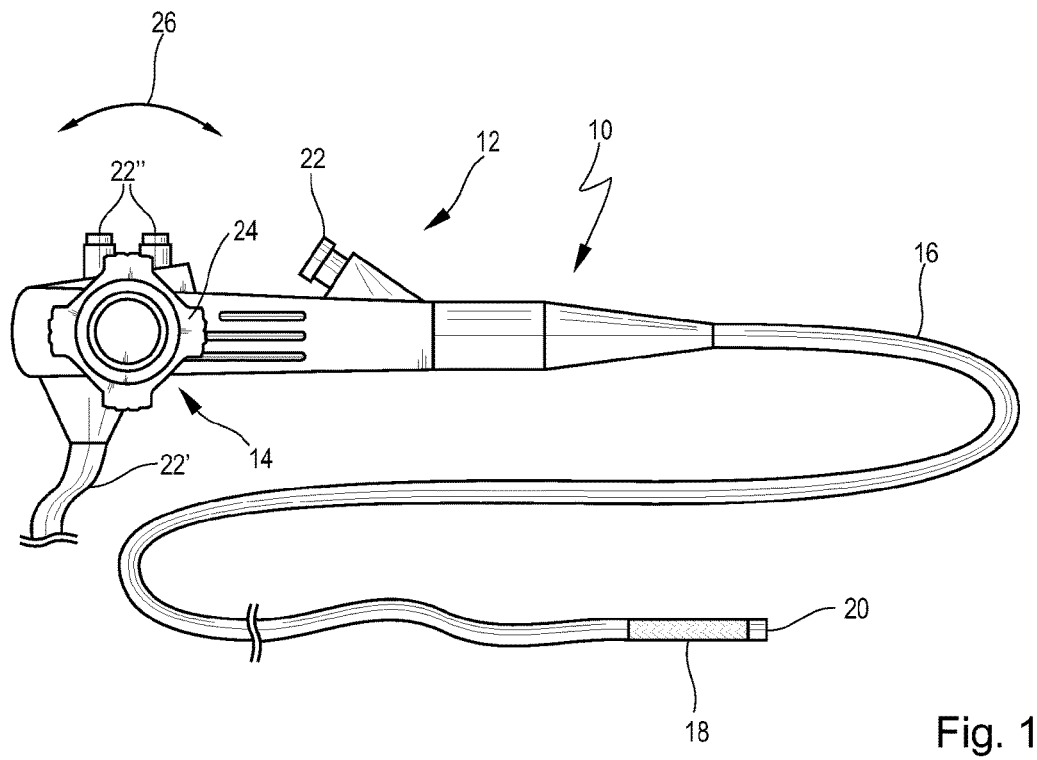
FIG. 1 shows an illustrative embodiment of a flexible endoscope with a deflectable distal portion.

FIG. 1 shows an endoscopic instrument 10 with a control section 12, with a control element 14 and a flexible instrument shaft 16. It will be noted that the explanations given within the context of the disclosure apply in the same way to a rigid instrument shaft (not shown).

The endoscopic instrument 10 is used for examining and/or surgical purposes in medical procedures. The instrument shaft 16 contains an endoscope optical system (not shown) in the form of light-guiding fibers, image carriers, various channels, such as a suction channel and flushing channel, and an instrument channel. The instrument shaft 16 is connected at the proximal end to the control section 12 and extends in the distal direction as far as a deflectable portion 18, which in this case is in particular an end portion.

The latter has an endpiece 20 in the form of a closure bushing. The endpiece 20 is the area of the instrument shaft 16 in which the light-guiding fibers, the image carriers and channels end. The instrument shaft 16 is shown only in part in the figures. The control section 12 has a connector 22, a supply cable 22' and buttons 22''. The connector 22 leads to an instrument channel. Instruments can be guided through it into the instrument shaft 16 and all the way through the endpiece 20. In this way, for example, operations can be performed in the area in front of the endpiece 20.

The supply cable 22' contains various types of supply lines, for example an electrical supply line, light guides, suction and flushing hoses and/or data links. The imaging of the endoscopic instrument 10 is effected via an image sensor (not shown) in the interior of the control section 12 or in the endpiece 20, wherein the image data is transmitted through the supply cable 22' to the outside, in particular to a camera control unit, or CCU (not shown).

To control the deflection of the portion 18, the control element 14 is provided, shown here in an embodiment with a handle 24 that can be turned in the directions of the double arrow 26. The deflectable portion 18 is deflected up/down or left/right when the control element 14 is turned. Here, the deflection corresponds in each case to the direction of rotation of the control element 14, i.e. either counterclockwise or clockwise. In a preferred embodiment, in addition to the control element 14 shown, a further control element (not shown) is used, such that up/down and left/right movements can be combined via a further adjustment element and a further pull element.

Figure 2:
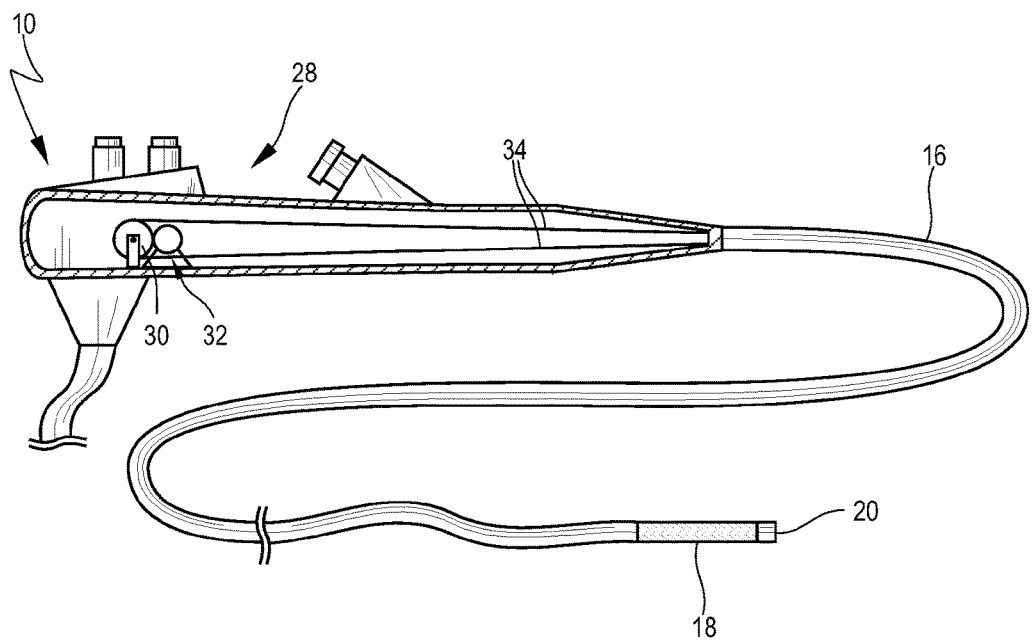
FIG. 2 shows the endoscope from FIG. 1 in a simplified schematic and partially cut-away sectional view.

As is shown in a very simplified manner in FIG. 2, an adjustment element 30 and an actuator 32 are arranged in a proximal end area 28 of the control section 12. The adjustment element 30 is connected to a pull element 34, which is guided through the instrument shaft 16 and extends into the end portion 18. The pull element 34 is guided around a part of the adjustment element 30 and is here configured in one piece.

Figure 3:
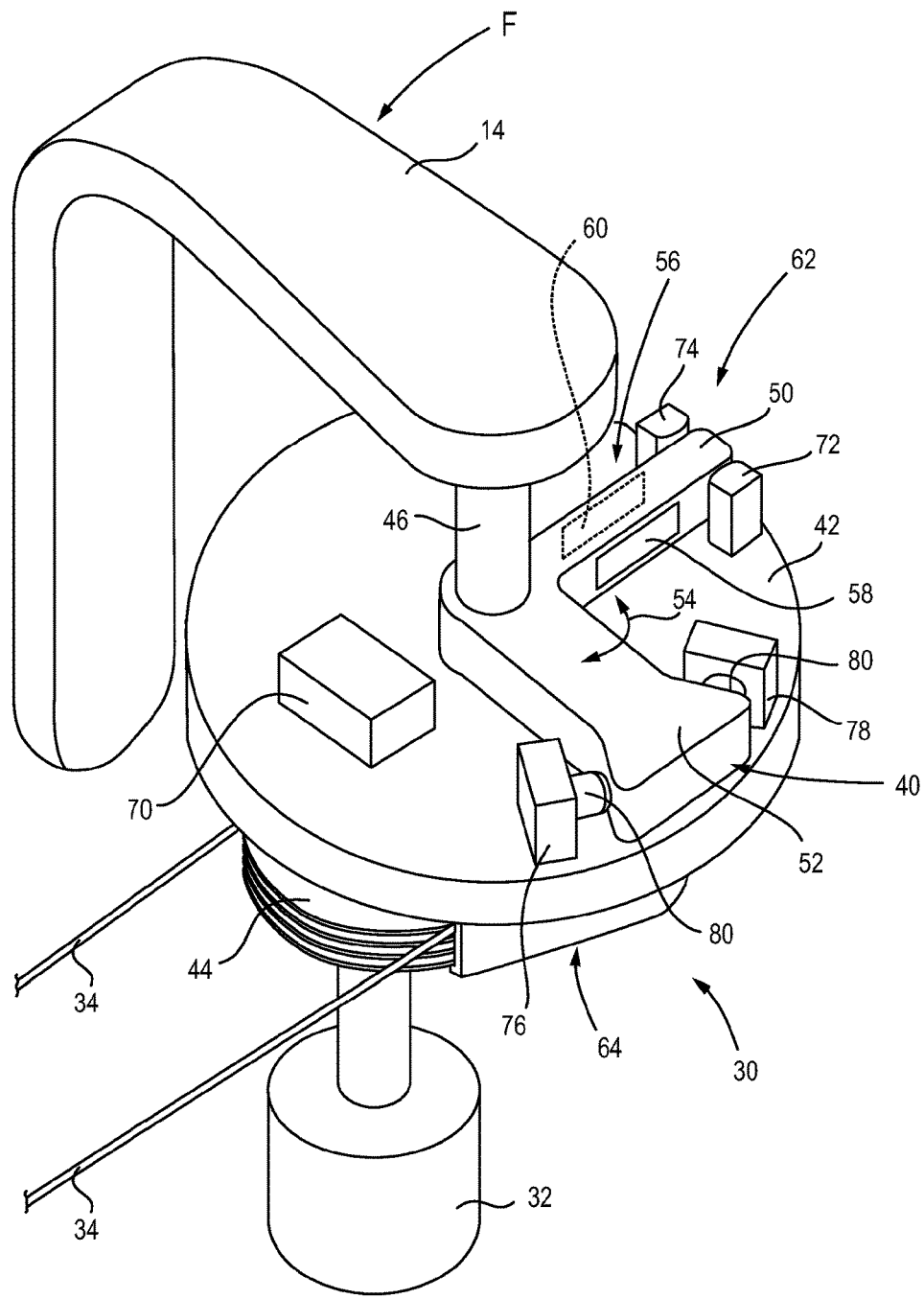
FIG. 3 shows a first embodiment of intermediate element and adjustment element.

FIG. 3 shows a first illustrative embodiment of an intermediate element 40 and of an adjustment element 30. The parts of the adjustment element 30 that can be seen here are an at least approximately circular support element 42 and a cord pulley 44.

The intermediate element 40 is fixedly connected to the control element 14 via a control lever shaft 46. The control element 14 is also operatively connected to the adjustment element 30, such that a force F applied to the control element 14 by the user can be transmitted to the adjustment element 30 via the intermediate element 40 in order to move the adjustment element 30, in particular here to move the cord pulley 44.

The intermediate element 40 has a first portion 50 and a second portion 52. The first portion 50 is connected to the second portion 52, here configured in one piece and from a common material. The second portion 52 has a greater bending resistance than the first portion 50, here in relation to a direction of movement 54 of the intermediate element 40.

The first portion 50 has a measurement element 56 for measuring a flexion of the first portion 50. The measurement element 56 here has a first measurement element part 58 and a second measurement element part 60. Since the second measurement element part 60 is concealed in this view by the first portion 50, it is indicated only by broken lines. As will be seen, the measurement element 56 is arranged on the first portion 50, and, in the event of a change of shape of the measurement element 56, the electrical resistance of the measurement element 56 changes. The measurement element 56, being specifically the first measurement element part 58 and the second measurement element part 60, is in each case preferably configured as a strain gauge.

As shown, the first measurement element part 58 and the second measurement element part 60 are arranged on two different sides of the first portion 50. This has the effect that, in the event of a flexion of the first portion 50, a change of shape of the first measurement element part 58 differs from a change of shape of the second measurement element part 60. Specifically, this means that a flexion of the first portion 50 leads in particular either to an extension of the first measurement element part 58 and a shortening of the second measurement element part 60, or to a shortening of the first measurement element part 58 and an extension of the second measurement element part 60.

The adjustment element 30 has a first abutment device 62 and a second abutment device 64, which are arranged on a support element 42 in this embodiment. As can be seen in particular from FIGS. 4 and 6, the first abutment device 62 defines a first movement range 66 of the first portion 50 relative to the adjustment element 30. The second abutment device 64 defines a second movement range 68 of the second portion 52 relative to the adjustment element 30. As will be shown below, the first movement range 66 is smaller than the second movement range 68. In this embodiment, the first portion 50 is constantly in mechanical contact with the first abutment device 62, such that the first movement range 66 is zero or almost zero.

The endoscopic instrument 10 also has a controller 70, which is configured to detect a measured value or a measured signal of a flexion of the first portion 50 and to trigger the actuator 32, here an electric motor, on the basis of the measured value or the measured signal. To make the figure clearer, the electrical connection lines between the controller 70 and the measurement element 56 are not shown. It is preferable for the electrical connection to be provided at least in part by a printed circuit board. The possible ways in which the actuator 32 is triggered, i.e. purely by motor, purely manually or by a combination of these, have already been explained in detail and will not be repeated here.

The first abutment device 62 and the second abutment device 64 are here arranged in the circumferential direction of the support element 42. The first abutment device 62 has a first driving dog 72 and a second driving dog 74, which are designed here as projections and between which an area of the first portion 50 comes to lie. The second abutment device 64 is adjustable in order to vary the second movement range 68 of the second portion 52 relative to the adjustment element 30. For this purpose, the second abutment device 64 has a first abutment element 76 and a second abutment element 78, which can each be adjusted via a symbolically indicated grub screw 80. The further the grub screws 80 are unscrewed from the respective abutment element 76, 78, the smaller the second movement range 68 becomes.

Figure 4:
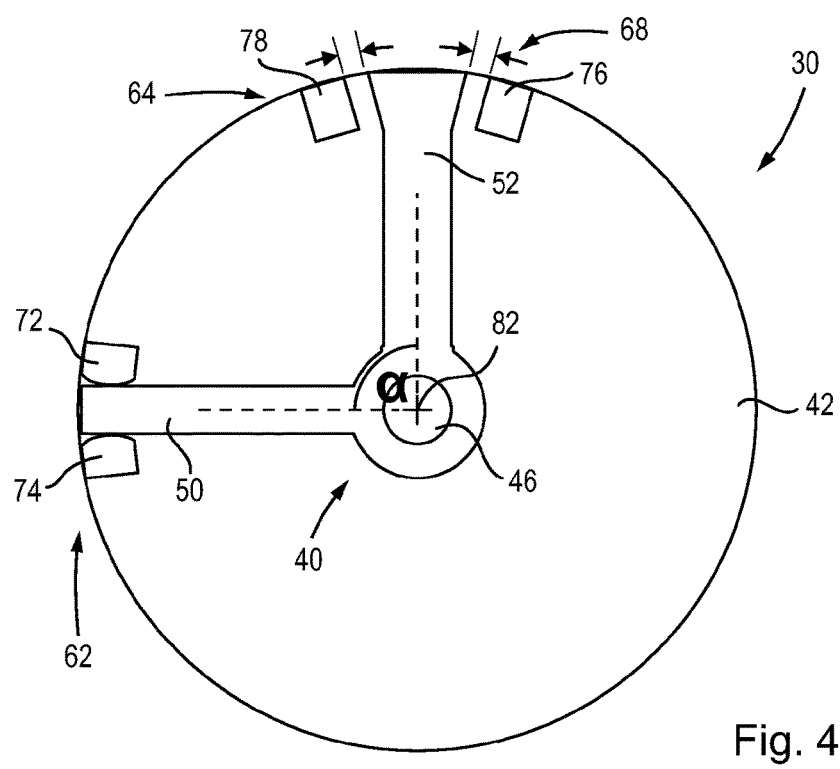
FIG. 4 shows a second embodiment of intermediate element and adjustment element in the rest state.

FIG. 4 shows a plan view of a second embodiment of intermediate element 40 and adjustment element 30, corresponding in terms of its function to the first embodiment according to FIG. 3.

As shown in the plan view the at least approximately beam-shaped portions 50, 52 converge on a common imaginary point 82 and, with respect to this common point 82, are at an angle α to each other. Here, the angle α is approximately 90°. If the intermediate element 40 is moved relative to the adjustment element 30 only to such an extent that the second movement range 68 is not exceeded, a flexion of the first portion 50 takes place only when the user applies a force F via the control element 14. The flexion is detected, and the actuator 32 is triggered to provide motorized movement of the adjustment element 30, here in particular of the cord pulley 44.

Figure 5:
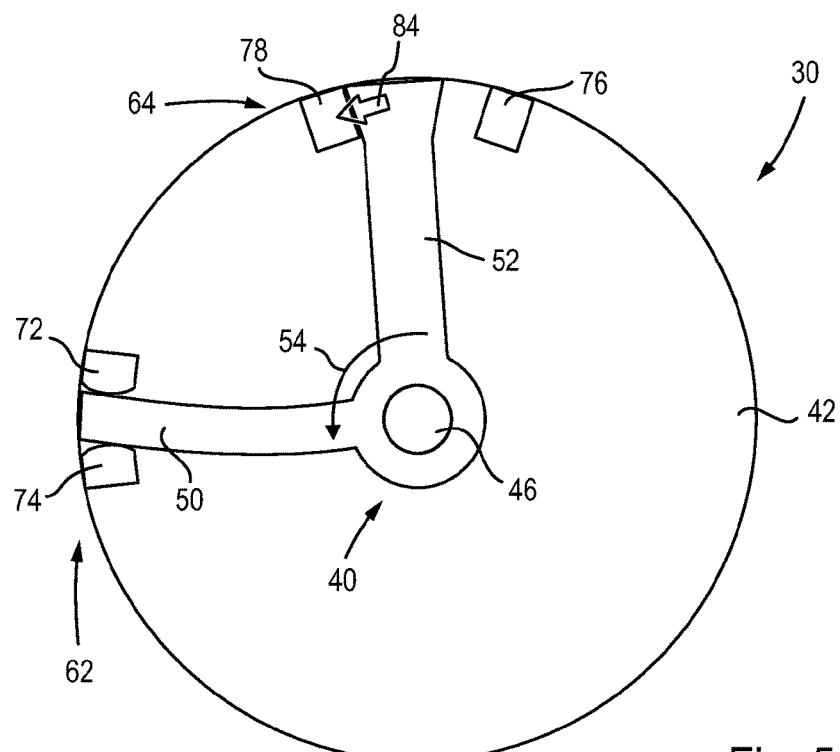
FIG. 5 shows the second embodiment in the deflected state.

FIG. 5 shows the second embodiment according to FIG. 4 when the force applied by the user is so great that the combined operation sets in. It will be seen that the first portion 50 is now bent and at least some of the force F applied by the user via the control element 14 is transmitted from the second portion 52 to the second abutment element 78 of the second abutment device 64. This is symbolized by means of the arrow 84. If the user further increases the force F, this force is transmitted substantially via the second portion 52 to the second abutment device 64 and does not lead to any further flexion, or any appreciable further flexion, of the first portion 50. This provides overload protection for the first portion 50.

Figure 6:
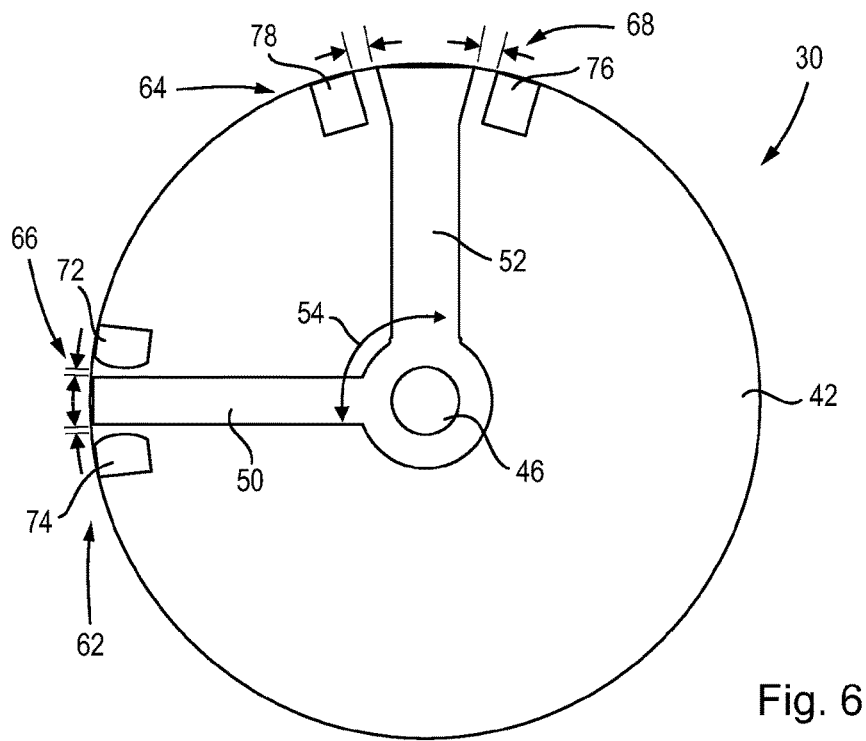
FIG. 6 shows a third embodiment of intermediate element and adjustment element.

FIG. 6 shows a third embodiment, which corresponds substantially to the embodiment according to FIG. 4, except that a visible first movement range 62 is now present. As has already been explained, care should be taken to ensure that the first movement range 62 is not greater than the second movement range 68, since otherwise a situation could arise in which only the purely manual mode of operation is available to the user, because the first portion 50 at no point experiences any flexion.

Figure 7:
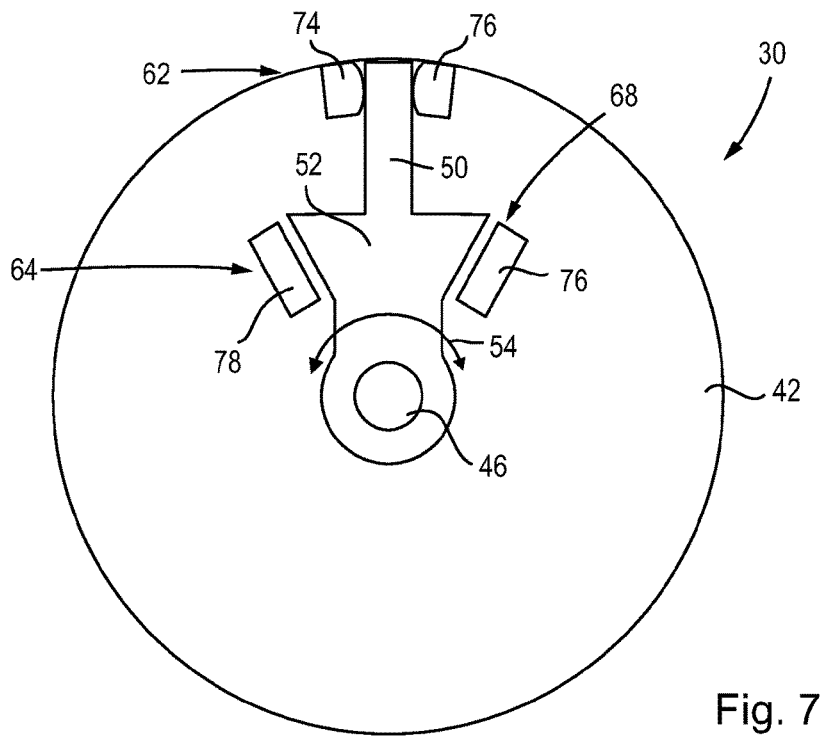
FIG. 7 shows a fourth embodiment of intermediate element and adjustment element.

FIG. 7 shows a fourth embodiment of intermediate element 40 and adjustment element 30. It will be seen here that the first portion 50 and second portion 52 can also be arranged one behind the other, i.e. along a straight line.

Figure 8:
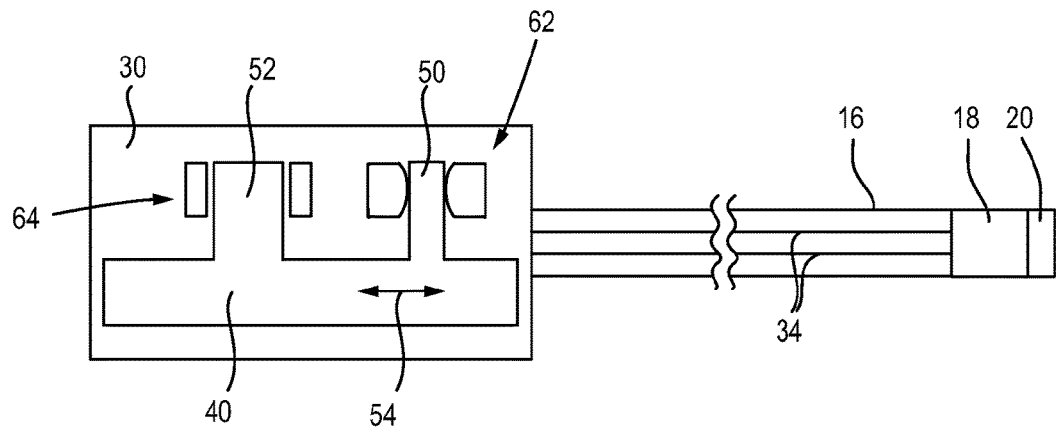
FIG. 8 shows a fifth embodiment of intermediate element and adjustment element.

FIG. 8 shows a fifth embodiment of intermediate element 40 and adjustment element 30. This illustrates a possibility of using the concept disclosed also for a linear movement. The actuator 32 (not shown) can also be designed here as an electric motor, in particular with the driven shaft of the electric motor having a toothed wheel which engages in a toothed rack on the adjustment element 30. A linear motor could also preferably be used.

Figure 9:
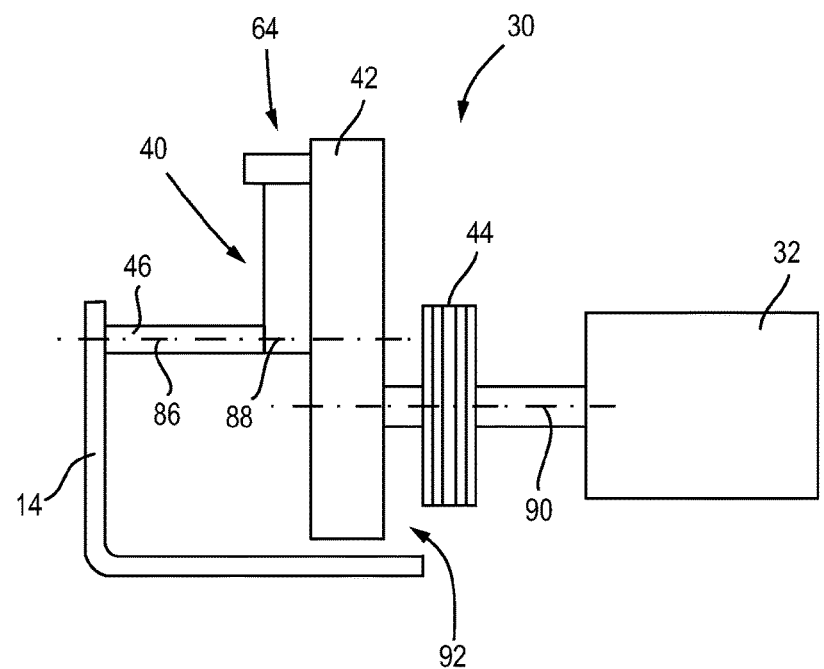
FIG. 9 shows a side view of a first embodiment of an arrangement of control element, intermediate element, adjustment element and actuator.

FIG. 9 shows a side view of a first embodiment of an arrangement of control element 14, intermediate element 40, adjustment element 30 and actuator 32. It will be seen here that a rotation axis 86 of the control element and a rotation axis 88 of the intermediate element 40 coincide. Moreover, a rotation axis 90 of the actuator is indicated. The adjustment element 30 has a gear 92 here. As is illustrated in the following figure, this gear is a step-up gear 92, i.e. a rotation of the control element 14 about a first angle leads to a greater rotation of the cord pulley 44.

Figure 10:
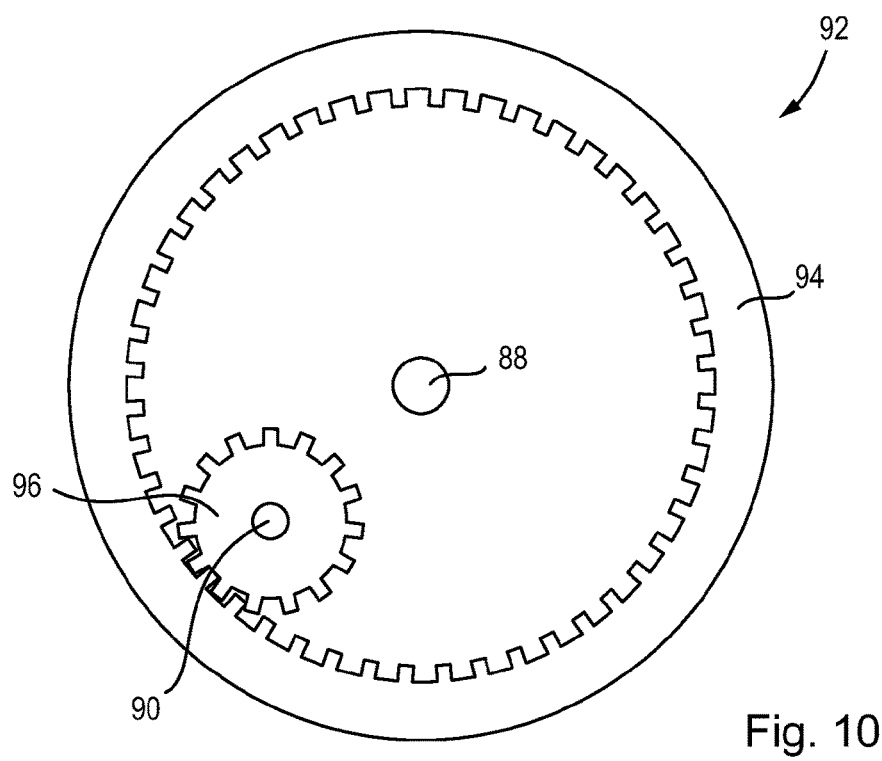
FIG. 10 shows a simplified view of the gear according to the sixth embodiment.

FIG. 10 shows an embodiment of the gear 92 according to FIG. 9. Here, the gear has an internal gear wheel 94 and a toothed wheel 96. By a suitable choice of the wheels 94, 96, a desired step-up can be easily obtained.

Figure 11:
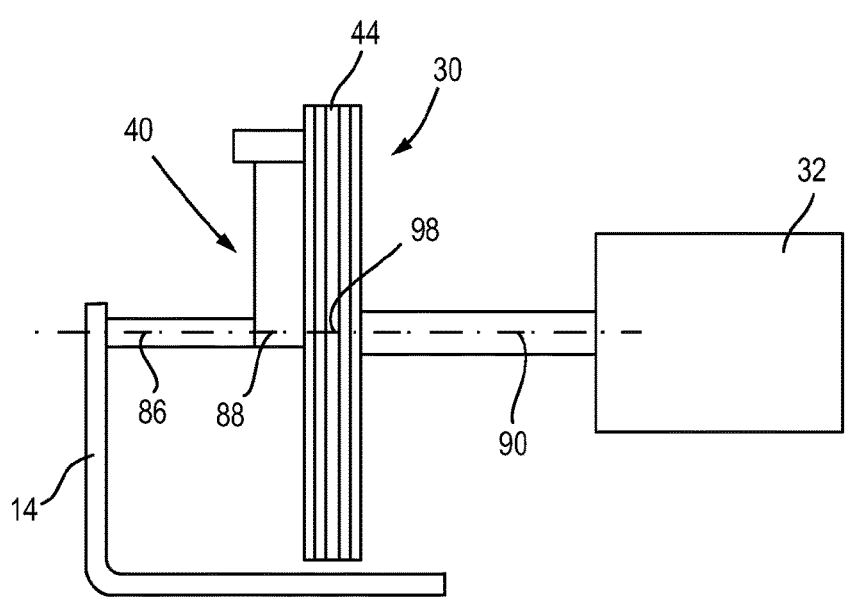
FIG. 11 shows a side view of a second embodiment of an arrangement of control element, intermediate element, adjustment element and actuator.

FIG. 11 shows a side view of a second embodiment of an arrangement of control element 14, intermediate element 40, adjustment element 30 and actuator 32. In this embodiment, the rotation axis 90 of the actuator 32 and a rotation axis 98 of the adjustment element 30 coincide. It will also be seen that the rotation axes 90, 98 also coincide with the rotation axes 86, 88. A further feature here is that the adjustment element 30 is configured as a cord pulley 44.

In summary, an endoscopic instrument 10 is disclosed that permits operation purely by motor, purely manually, or by a combination of the two. Moreover, in the event of a fault, it is ensured that the user can safely use the endoscopic instrument 10 without interruption and without restriction, despite lack of assistance from the actuator 32.

What is claimed is:

1. An endoscopic instrument, comprising:
a control section having a control element;
an instrument shaft having an actuatable portion, wherein the instrument shaft is connected to the control section;
an adjustment element;
a pull element, which is mechanically coupled to the adjustment element and to the actuatable portion of the instrument shaft, such that a movement of the adjustment element can cause an actuation of the actuatable portion via a force transmission via the pull element;
an actuator, which is coupled to the adjustment element, such that an actuation of the actuator can cause a movement of the adjustment element by force transmission from the actuator to the adjustment element; and
an intermediate element, which is operatively connected to the control element and to the adjustment element such that a force F applied to the control element by a user can be transmitted to the adjustment element via the intermediate element in order to move the adjustment element;
wherein the intermediate element has a first portion and a second portion, the first portion is connected to the second portion, the second portion having a greater bending resistance than the first portion, and the first portion having a measurement element configured to measure a flexion of the first portion;
wherein the adjustment element has a first abutment device, which defines a first movement range of the first portion relative to the adjustment element, and a second abutment device, which defines a second movement range of the second portion relative to the adjustment element, wherein the first movement range is smaller than the second movement range; and
wherein the first portion is configured to contact the first abutment device.

2. The endoscopic instrument of claim 1, wherein the first portion and the second portion are formed in one piece, in particular made from exactly one material.

3. The endoscopic instrument of claim 1, wherein the first portion and the second portion are made of exactly one material.

4. The endoscopic instrument of claim 1, wherein the first portion is continuously in mechanical contact with the first abutment device.

5. The endoscopic instrument of claim 1, wherein the measurement element is arranged on the first portion.

6. The endoscopic instrument of claim 1, wherein an electrical resistance of the measurement element changes in an event of a change of shape of the measurement element.

7. The endoscopic instrument of claim 1, wherein the measurement element has a first measurement element part and a second measurement element part, which are arranged on two different sides of the first portion in such a way that, in the event of a flexion of the first portion, a change of shape of the first measurement element part differs from a change of shape of the second measurement element part.

8. The endoscopic instrument of claim 1, wherein the second abutment device is adjustable in order to vary the second movement range of the second portion relative to the adjustment element.

9. The endoscopic instrument of claim 1, wherein the adjustment element comprises a gear.

10. The endoscopic instrument of claim 1, wherein the adjustment element comprises a gear with a positive transmission ratio.

11. The endoscopic instrument of claim 1, wherein a first rotation axis of the adjustment element and a second rotation axis of the actuator coincide.

12. The endoscopic instrument of claim 1, wherein the adjustment element has an at least approximately circular support element, on which the first abutment device and the second abutment device are arranged.

13. The endoscopic instrument of claim 12, wherein the first abutment device and the second abutment device are arranged on the support element at least approximately in a circumferential direction of the support element.

14. The endoscopic instrument of claim 1, further comprising a controller configured to detect a measured value of a flexion of the first portion and to trigger the actuator on the basis of the measured value.

15. The endoscopic instrument of claim 1, wherein a third rotation axis of the control element and a rotation axis of the intermediate element coincide.

16. The endoscopic instrument of claim 1, wherein the measurement element has at least one strain gauge.

17. The endoscopic instrument of claim 1, wherein the first portion and the second portion are configured at least approximately in a beam shape, converge on a common point and, in relation to this common point, are at an angle $\alpha$ to each other.

18. An endoscopic instrument, comprising:
a control section having a control element;
an instrument shaft having an actuatable portion, wherein the instrument shaft is connected to the control section;
an adjustment element;
a pull element, which is mechanically coupled to the adjustment element and to the actuatable portion of the instrument shaft;
an actuator coupled to the adjustment element; and
an intermediate element, which is operatively coupled with the control element and to the adjustment element;
wherein the intermediate element has a first portion and a second portion, the first portion is connected to the second portion, the second portion having a greater bending resistance than the first portion, and the first portion has a measurement element configured to measure a flexion of the first portion;
wherein the adjustment element has a first abutment device defining a first movement range of the first portion relative to the adjustment element, and a second abutment device defining a second movement range of the second portion relative to the adjustment element, the first movement range being smaller than the second movement range; and
wherein the first portion is configured to contact the first abutment device.

19. The endoscopic instrument of claim 1, wherein the second portion is moveable relative to the second abutment device between a first position, in which the second portion is in contact with the second abutment device, and a second position, in which a distance extends between the second portion and the second abutment device.

20. The endoscopic instrument of claim 18, wherein the second portion is moveable relative to the second abutment device between a first position, in which the second portion is in contact with the second abutment device, and a second position, in which a distance extends between the second portion and the second abutment device.

* * * * *